(12) United States Patent
Jiang et al.

(10) Patent No.: US 10,088,424 B2
(45) Date of Patent: Oct. 2, 2018

(54) TAPERED OPTICAL NEEDLE

(71) Applicants: Industrial Technology Research Institute, Hsinchu (TW); National Tsing Hua University, Hsinchu (TW)

(72) Inventors: Ruei-Han Jiang, Taoyuan (TW); Jen-You Chu, Hsinchu (TW); Ta-Jen Yen, Hsinchu (TW)

(73) Assignees: Industrial Technology Research Institute, Hsinchu (TW); National Tsing Hua University, Hsinchu (TW)

( * ) Notice: Subject to any disclaimer, the term of this patent is extended or adjusted under 35 U.S.C. 154(b) by 0 days.

(21) Appl. No.: 15/390,525

(22) Filed: Dec. 25, 2016

(65) Prior Publication Data

US 2018/0059025 A1 Mar. 1, 2018

Related U.S. Application Data (60) Provisional application No. 62/378,684, filed on Aug. 24, 2016.

(30) Foreign Application Priority Data

Dec. 20, 2016 (TW) .............................. 105142127 A (51) Int. Cl.
*G01N 21/65* (2006.01)
*G01Q 60/22* (2010.01)
(Continued)

(52) U.S. Cl.
CPC ........... *G01N 21/658* (2013.01); *G01Q 60/22* (2013.01); *G02B 5/008* (2013.01);
(Continued)

(58) Field of Classification Search
CPC ...... G01N 21/658; G01Q 60/00; G01Q 60/06; G01Q 60/18; G01Q 60/20; G01Q 60/22;
(Continued)

(56) References Cited

U.S. PATENT DOCUMENTS 6,236,783 B1 * 5/2001 Mononobe ............. G01B 11/30
385/123
6,408,123 B1 6/2002 Kuroda et al.
(Continued)

FOREIGN PATENT DOCUMENTS

| CN | 101447235 | 9/2010 |
| CN | 103176283 | 11/2014 |

(Continued)

OTHER PUBLICATIONS

H. A. Bethe, "Theory of Diffraction by Small Holes," The Physical Review, Oct. 1, 1944, pp. 163-182.
(Continued)

*Primary Examiner* — Jason McCormack
(74) *Attorney, Agent, or Firm* — JCIPRNET (57) ABSTRACT

A tapered optical needle includes a tapered light-transmissive needle and a surface plasmon wave transport layer. The tapered light-transmissive needle has a first tip, a bottom, and a curved surface connecting the first tip and the bottom. The surface plasmon wave transport layer is disposed on the curved surface and covers the first tip, wherein the surface plasmon wave transport layer has a curved slit structure. The curved slit structure includes a plurality of curved portions arranged from the first tip to an edge of the bottom and located between the first tip and the edge of the bottom, and extending directions of the curved portions are different to a direction from the first tip to the edge of the bottom.

13 Claims, 9 Drawing Sheets

(51) Int. Cl.
 *G02B 5/00* (2006.01)
 *G02B 6/122* (2006.01)
(52) U.S. Cl.
 CPC ...... *G01N 2021/656* (2013.01); *G02B 6/1226* (2013.01); *G02B 6/1228* (2013.01)
(58) Field of Classification Search
 CPC ........ G01Q 70/08; G01Q 70/10; G01Q 70/12; G01Q 70/14; G01Q 70/16
 USPC ........ 850/21, 24, 29, 30, 31, 32, 56, 57, 58, 850/59, 60
 See application file for complete search history.

(56) References Cited

U.S. PATENT DOCUMENTS

| | | | |
|---|---|---|---|
| 6,834,027 | B1 | 12/2004 | Sakaguchi et al. |
| 7,054,528 | B2 | 5/2006 | Blumberg |
| 7,250,598 | B2 | 7/2007 | Hollingsworth et al. |
| 8,490,210 | B2 | 7/2013 | Hahn |
| 2005/0031278 | A1 | 2/2005 | Shi et al. |
| 2005/0289576 | A1 | 12/2005 | Challener |
| 2006/0076474 | A1 | 4/2006 | Lapchuk et al. |
| 2008/0185521 | A1* | 8/2008 | Hollingsworth ....... B82Y 20/00 250/338.1 |
| 2010/0017922 | A1* | 1/2010 | Shin ........................ B82Y 20/00 850/21 |
| 2011/0279817 | A1* | 11/2011 | Amako ................ G01N 21/554 356/301 |
| 2011/0321204 | A1 | 12/2011 | Karaki et al. |
| 2014/0141555 | A1 | 5/2014 | Lowgren |

FOREIGN PATENT DOCUMENTS

| | | |
|---|---|---|
| CN | 103837709 | 3/2016 |
| EP | 2335053 | 6/2011 |
| JP | 2007155453 | 6/2007 |
| JP | 2007155454 | 6/2007 |
| TW | 201319627 | 5/2013 |
| TW | 201419569 | 5/2014 |
| TW | I461741 | 11/2014 |
| TW | 201511334 | 3/2015 |
| WO | 2008025491 | 3/2008 |

OTHER PUBLICATIONS

Zenhausern et al., "Apertureless Near-Field Optical Microscope," Applied Physics Letters, Sep. 26, 1994, pp. 1623-1625.

Jin et al., "Finitte-Difference Time-Domain Studies on Optical Transmission through Planar Nano-Apertures in a Metal Film," Japanese Journal of Applied Physics, Jan. 13, 2004, pp. 407-417.

Wang et al., "Plasmonic Nearfield Scanning Probe with High Transmission, " Nano Letters, Aug. 23, 2008, pp. 3041-3045.

Neacsu et al., "Near-Field Localization in Plasmonic Superfocusing: A Nanoemitter on a Tip," Nano Letters, Jan. 12, 2010, pp. 592-596.

Cherukulappurath et al., "Template-Stripped Asymmetric Metallic Pyramids for Tunable Plasmonic Nanofocusing," Nano Letters, Oct. 21, 2013, pp. 5635-5641.

Lee et al., "Designs of apertureless probe with nano-slits for near-field light localization and concentration, " Optics Communications, Apr. 3, 2012, pp. 3373-3377.

Lee et al., "Efficient apertureless scanning probes using patterned plasmonic surfaces," Optics Express, Dec. 6, 2011, pp. 25990-25999.

Barnes et al., "Surface plasmon subwavelength optics, " Nature, Aug. 14, 2003, pp. 824-830.

Srituravanich et al., "Flying plasmonic lens in the near field for high-speed nanolithography," Nature Islanotechnology, Dec. 2008, pp. 733-737.

Zhang et al., "Chemical Mapping of a Single Molecule by Plasmon-Enhanced Raman Scattering," Nature, Jun. 6, 2013, pp. 82-86.

Tugchin et al., "Plasmonic Tip Based on Excitation of Radially Polarized Conical Surface Plasmon Polariton for Detecting Longitudinal and Transversal Fields," ACS Photonics, Oct. 5, 2015, pp. 1468-1475.

Angelis et al., "Nanoscale chemical mapping using three-dimensional adiabatic compression of surface plasmon polaritons," Nature Nanotechnology, Jan. 2010, pp. 67-72.

Wang et al., "Plasmonic nanograting tip design for high power throughput near-field scanning aperture probe," Optics Express, Jun. 15, 2010, pp. 14004-14011.

Ropers et al., "Grating-Coupling of Surface Plasmons onto Metallic Tips: A Nanoconfined Light Source," Nano Letters, Aug. 9, 2007, pp. 2784-2788.

Umakoshi et al., "Highly efficient plasmonic tip design for plasmon nanofocusing in near-field optical microscopy," Nanoscale, Feb. 15, 2016, pp. 5634-5640.

"Office Action of Taiwan Counterpart Application," dated Dec. 26, 2017, p. 1-p. 4.

"Search Report of Europe Counterpart Application", dated Nov. 29, 2017, p. 1-p. 11.

* cited by examiner

TAPERED OPTICAL NEEDLE

CROSS-REFERENCE TO RELATED APPLICATION

This application claims the priority benefits of U.S. provisional application Ser. No. 62/378,684, filed on Aug. 24, 2016 and Taiwan application serial no. 105142127, filed on Dec. 20, 2016. The entirety of each of the above-mentioned patent applications is hereby incorporated by reference herein and made a part of this specification.

TECHNICAL FIELD

The disclosure relates to an optical structure, and particularly relates to a tapered optical needle.

BACKGROUND

Along with development of technology, sizes of materials and components have been reduced to a nanoscale, and people have entered a new nanotechnology era. In various nanotechnology developments, nano microscopy technique and nano manipulation technique have attracted extensive attention, and based on the aforementioned techniques, atoms, molecules or molecule arrangement can be controlled according to material characteristics, and new techniques applied to human life can be further created, for example, an optical lithography technique, a nanomaterial sensing technique, micro drag detection, DNA detection, etc. However, in development of optical technology, since an optical lens is limited by Abbe's diffraction limit, a size of a light source can only be about several hundreds of nanometers or more, which greatly limits the development of the optical technology. On the other hand, in the optical detection technique, since a difference between sizes of a light source and a nano substance is too large, efficiency of an interaction force between light and the nano substance is decreased, which causes inadequate sensitivity of the optical detection, for example, a weak Raman signal. Therefore, under the current nanotechnology development, it is one of the popular research trends to develop a stable nanometer light source.

In the current nanotechnology development, research of surface plasmon occupies an important position. The surface plasmon is a collective electron gas resonance wave existing at the interface between a metal and a dielectric, and such resonance wave may produce an electromagnetic field nanofocus effect to form a nano light source through a specific structure design, wherein the nano light source has a nanoscale, and may produce a high efficiency interaction force with a substance with the nanoscale, so that sensitivity of the optical detection is improved to reach a single molecule level. In a daily life level, the nano light source technology can be applied to detect contaminants in environment and food such as plasticizers, environmental hormones, phosphates, etc., or applied to biomedical field detection, for example, non-dye based biological calibration, antigen detection, DNA synthesis, drug or biological screening and tissue testing, etc. Moreover, in the field of microscope, the nano light source technology can be combined with a tip enhanced Raman spectroscopy (TERS) method for applying to an atomic force microscope (AFM), in this way, such device has both of sensitivity of surface-enhanced Raman spectroscopy (SERS) and an ultra high spectral resolution provided by the AFM.

In current development of nano light source structure, a front end of a needle-like structure of a probe is opened by 100 nm, and the nanoscale light source is produced at a near-field of the opening, though a light intensity of the nanoscale light source of such structure is limited by Bethe's theory, such that a light flux of the nano light source only has a light conversion efficiency of $10^{-5}$ to $10^{-7}$ to decrease a signal to noise ratio. In order to maintain an enough signal to noise ratio to decrease a measuring time or an lithography exposure time, an actual size of an aperture of such structure is about 50 to 100 nm, which results in a fact that the optical resolution is only 50 to 100 nm and a spatial resolution is greater than 100 nm.

SUMMARY

The disclosure is directed to a tapered optical needle, where a nano light source is produced at a tip thereof through an excitation light source, so as to improve a resolution and a light emitting gain, or an optical signal is received by the tip to improve a measuring resolution.

An embodiment of the disclosure provides a tapered optical needle including a tapered light-transmissive needle and a surface plasmon wave transport layer. The tapered light-transmissive needle has a first tip, a bottom, and a curved surface connecting the first tip and the bottom. The surface plasmon wave transport layer is disposed on the curved surface and covers the first tip, wherein the surface plasmon wave transport layer has a curved slit structure. The curved slit structure includes a plurality of curved portions arranged from the first tip to an edge of the bottom and located between the first tip and the edge of the bottom, and extending directions of the curved portions are different to a direction from the first tip to the edge of the bottom.

In the tapered optical needle of the embodiment of the disclosure, the surface plasmon wave transport layer has the curved slit structure, so as to induce a surface plasmon wave on the surface plasmon wave transport layer. In this way, the tapered optical needle of the embodiment of the disclosure is adapted to transport the surface plasmon wave to the tip of the tapered optical needle, and form a nanofocus effect at the tip to produce a high efficiency nanoscale light source, so as to improve the resolution and light emitting gain. Alternatively, the tapered optical needle of the disclosure is adapted to receive an optical signal from the tip of the tapered optical needle, so as to improve a measuring resolution.

In order to make the aforementioned and other features and advantages of the disclosure comprehensible, several exemplary embodiments accompanied with figures are described in detail below.

DESCRIPTION OF EMBODIMENTS

Figure 1:
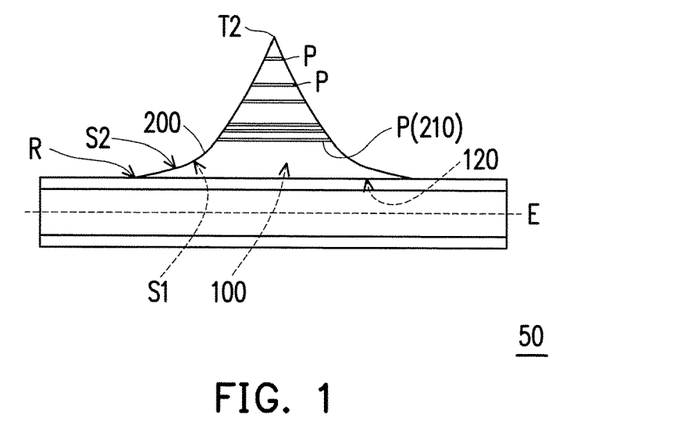
FIG. 1 is a side view of a tapered optical needle according to an embodiment of the disclosure.
Figure 2:
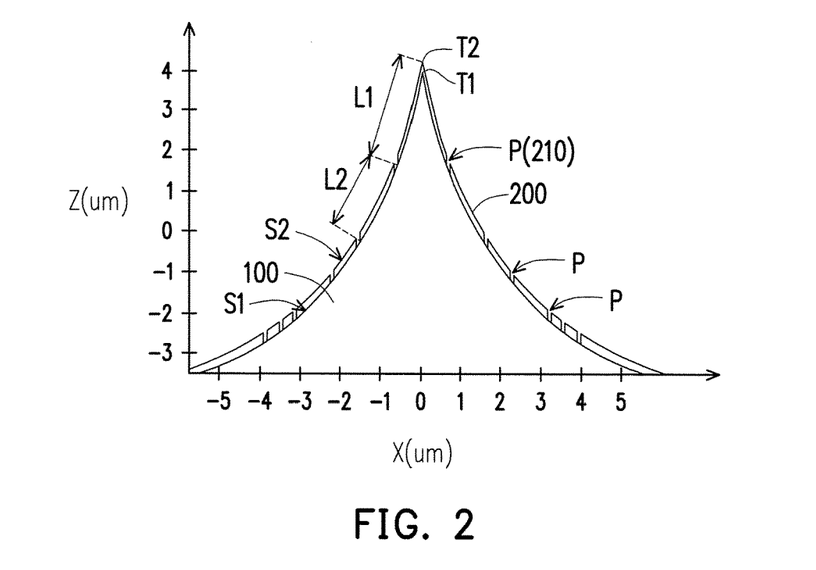
FIG. 2 is a cross-sectional view of the tapered optical needle of FIG. 1.

FIG. 1 is a side view of a tapered optical needle according to an embodiment of the disclosure. FIG. 2 is a cross-sectional view of the tapered optical needle of FIG. 1. Referring to FIG. 1 and FIG. 2, in an embodiment of the disclosure, the tapered optical needle 50 includes a tapered light-transmissive needle 100 and a surface plasmon wave transport layer 200. The tapered light-transmissive needle 100 has a first tip T1, a bottom 120, and a curved surface S1 connecting the first tip T1 and the bottom 120. To be specific, the tapered light-transmissive needle 100 of the present embodiment is a circularly symmetric tapered structure, and the curved surface S1 is a tapered surface of the tapered light-transmissive needle 100. The tapered surface can be a quasi-parabolic surface, a conic surface, or other circularly symmetric tapered curved surfaces, and in the present embodiment, the curved surface S1 is, for example, a quasi-parabolic surface, as shown in FIG. 1, though the disclosure is not limited thereto.

Figure 3A:
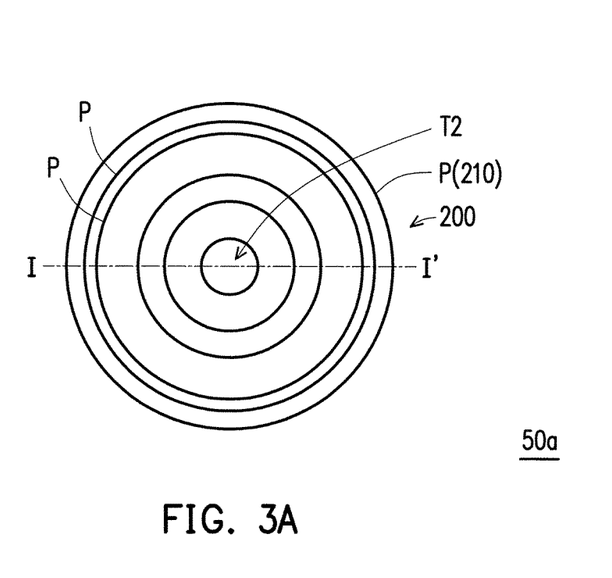
FIG. 3A is a top view of the tapered optical needle of FIG. 1.
Figure 3B:
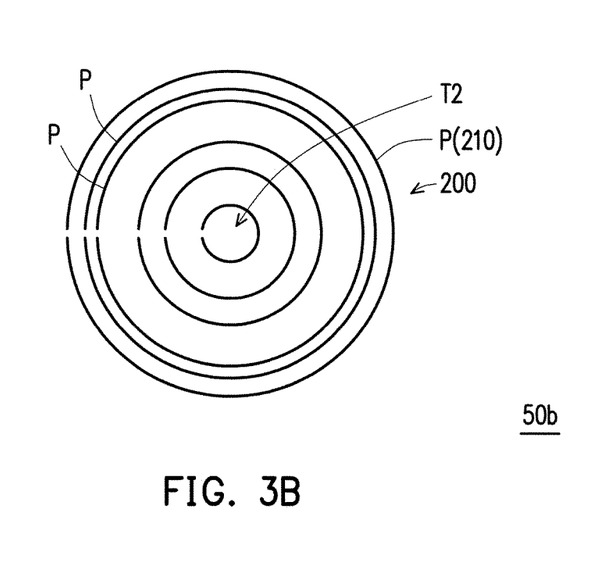
FIG. 3B and FIG. 3C are top views of a tapered optical needle according to another embodiment.
Figure 3C:
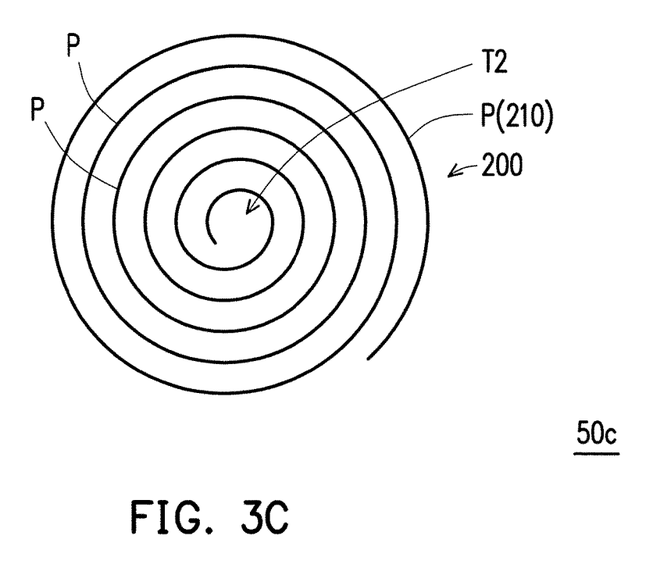
Figure 4:
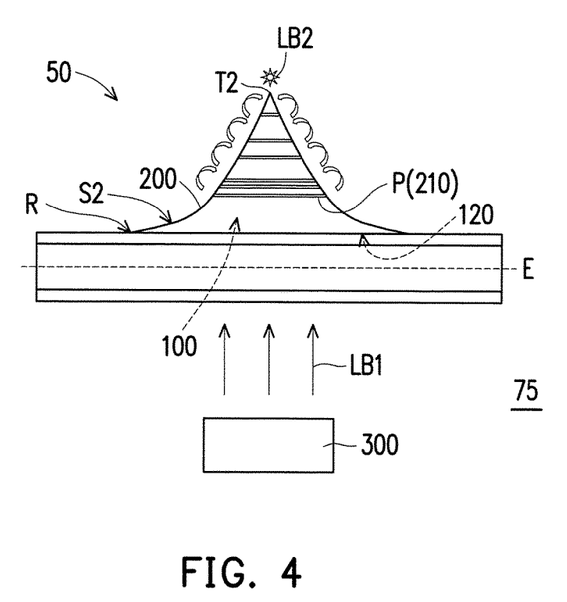
FIG. 4 is a schematic diagram of a light source device having the tapered optical needle of FIG. 1.

FIG. 3A is a top view of the tapered optical needle of FIG. 1. FIG. 3B and FIG. 3C are top views of a tapered optical needle according to other embodiments of the disclosure. FIG. 4 is a schematic diagram of a light source device having the tapered optical needle of FIG. 1. Referring to FIG. 2 to FIG. 4, in the present embodiment, the light source device 75 includes a tapered optical needle 50 and an excitation light source 300 used for emitting an exciting beam LB1 to the tapered optical needle 50, wherein the surface plasmon wave transport layer 200 is disposed on the curved surface S1. To be specific, the surface plasmon wave transport layer 200 covers the first tip T1 and the curved surface S1 of the tapered light-transmissive needle 100. The surface plasmon wave transport layer 200 has a curved slit structure 210. To be specific, the curved slit structure 210 is actually a gap, as shown in FIG. 2. Therefore, the internal tapered light-transmissive needle 100 may simultaneously contact the surface plasmon wave transport layer 200 and air through the gap. When the excitation light source 300 provides a radial polarized light entering the tapered light-transmissive needle 100 from the bottom 120, a surface plasmon wave is induced at the curved slit structure 210, and the surface plasmon wave is transported on an outer surface S2 of the surface plasmon wave transport layer 200 facing away from the tapered light-transmissive needle 100. In the present embodiment, a material of the tapered light-transmissive needle 100 includes silicon dioxide, for example, glass with a main component of silicon dioxide, and a material of the surface plasmon wave transport layer 200 may be metal, for example, gold, silver, aluminium, etc., which is adapted to a situation that the exciting beam LB1 is a visible light beam since the silicon dioxide is a transparent material for the visible light. In other embodiments, the material of the tapered light-transmissive needle 100 includes silicon, for example, a main component thereof is silicon, and the material of the surface plasmon wave transport layer 200 can be made of a semiconductor material, for example, silicon carbide, which is adapted to a situation that the exciting beam LB1 is an infrared light beam since silicon is a transparent material for the infrared light, though the disclosure is not limited thereto.

Moreover, in the present embodiment, a thickness of the surface plasmon wave transport layer 200 is greater than a penetration depth D that the exciting beam LB1 penetrates through the surface plasmon wave transport layer 200, and the penetration depth D satisfies:

$$D = \frac{\lambda}{4\pi(n''_{sp})},$$

wherein $\lambda$ is a wavelength of the exciting beam LB1, $n''_{sp}$ is an imaginary part of a refractive index of the surface plasmon wave transport layer 200. A slit width B of the curved slit structure 210 satisfies:

$$B < \frac{\lambda}{2},$$

in other words, the slit width B of the curved slit structure 210 is smaller than a half wavelength of the exciting beam LB1, by which a light transmittance of the slit is decreased to reduce noise, though the disclosure is not limited thereto.

On the other hand, the curved slit structure 210 includes a plurality of curved portions P arranged from the first tip T1 to an edge R of the bottom 120 and located between the first tip T1 and the edge R of the bottom 120, and extending directions of the curved portions P are different to a direction from the first tip T1 to the edge R of the bottom 120. To be specific, the curved slit structure 210 is a circularly symmetric ring-like slit extending to form a circle, as that shown in FIG. 3A. However, in other embodiments, viewing from a top view, the curved slit structure 210 can be a continuous spiral slit (as shown in FIG. 3C), or can be constructed by a plurality of C-shape ring-like slits with different radiuses by taking the first tip T1 as a common center. In the present embodiment, the ring-like slit is taken as an example for description, as shown in FIG. 3A, though the disclosure is not limited thereto. Besides, in other embodiments, a distance between a center of an orthogonal projection of the curved slit structure 210 on a reference plane E parallel to the bottom 120 and an orthogonal projection of the first tip T1 on the reference plane E is not more than 1/10 of the wavelength of the exciting beam LB1 used for driving the tapered optical needle 50. For example, taking the ring-shape structure as an example, a distance between an orthogonal projection of a center of the ring-shape structure on the reference plane E and an orthogonal projection of the first tip T1 on the reference plane E can be within 1/10 of the wavelength of the exciting beam LB1, though the disclosure is not limited thereto.

On the other hand, one end of the surface plasmon wave transport layer 200 facing away from the first tip T1 is a second tip T2, and among the curved portions P arranged from the first tip T1 of the tapered light-transmissive needle 100 to the edge R of the bottom 120, a distance between the second tip T2 and the curved portion P closest to the second tip T2 and distances between the adjacent curved portions P are all different. In brief, the distances between the adjacent curved portions P arranged from the first tip T to the edge R of the bottom 120 are specific distances, and the distances are different to each other, so as to produce a surface plasmon resonance. Namely, the curved portions P are located at the positions producing the surface plasmon resonance at the outer surface S2 of the surface plasmon wave transport layer 200. In detail, the actual positions of the curved portions P are determined one-by-one outward from the center by a two-dimensional simulation program according to an appearance of the outer surface S2 of the curved slit structure 210, and then an optimal electromagnetic field strength produced at the second tip T2 is simulated by a three-dimensional simulation program. For example, a distance L1 between the second tip T2 and the curved portion P closest to the second tip T2 is 10 times the half wavelength of the surface plasmon wave; a distance L2 between the curved portion P closest to the second tip T2 and the curved portion P secondly closest to the second tip T2 is 6 times the half wavelength of the surface plasmon wave; a distance L3 between the curved portion P secondly closest to the second tip T2 and the curved portion P thirdly closest to the second tip T2 is 3 times the half wavelength of the surface plasmon wave; a distance L4 between the curved portion P thirdly closest to the second tip T2 and the curved portion P fourthly closest to the second tip T2 is 4 times the half wavelength of the surface plasmon wave; a distance L5 between the curved portion P fourthly closest to the second tip T2 and the curved portion P fifthly closest to the second tip T2 is one time the half wavelength of the surface plasmon wave; and a distance L6 between the curved portion P fifthly closest to the second tip T2 and the curved portion P sixthly closest to the second tip T2 is 2 times the half wavelength of the surface plasmon wave, as shown in FIG. 2 (only L1 and L2 are illustrated). In other words, the distance between the second tip T2 and the curved portion P closest to the second tip T2 and the distances between every adjacent curved portions P can be positive integer multiples of the half wavelength of the excited surface plasmon wave. On the other hand, the distance L between the second tip T2 and each of the curved portions P arranged from the second tip T2 to the edge R of the bottom 120 in the curved slit structure 210 satisfies:

$$0 < L \le \frac{1}{2k''_{sp}}, \text{ and } k_{sp} = k'_{sp} + ik''_{sp} = \left[\frac{\omega}{c}\left(\frac{\varepsilon_1\varepsilon_2}{\varepsilon_1+\varepsilon_2}\right)^{1/2}\right],$$

wherein $k_{sp}$ is a wave vector constant of the surface plasmon wave, $k'_{sp}$ and $ik''_{sp}$ are respectively a real part and an imaginary part of $k_{sp}$, $\omega$ is a frequency of the excitation light source, C is the light speed, $\varepsilon_1$ is a dielectric coefficient of the surface plasmon wave transport layer, $\varepsilon_2$ is a real part of a dielectric coefficient of the tapered light-transmissive needle 100. The position setting of the curved slit structure 210 and the curved portions P therein optimized by the simulation programs may greatly improve a focusing effect of the tapered optical needle 50, and an electric field enhancement strength thereof is far greater than that of a general mainstream optical probe.

Figure 5A:
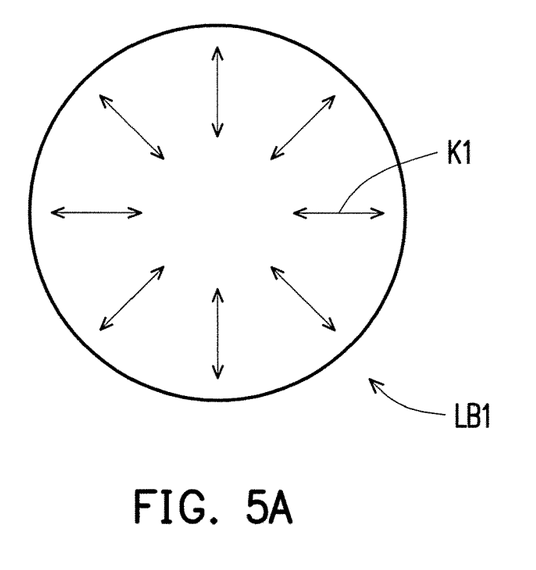
FIG. 5A and FIG. 5B are respectively schematic diagrams of cross sections of a radial polarized light and a linear polarized light.
Figure 5B:
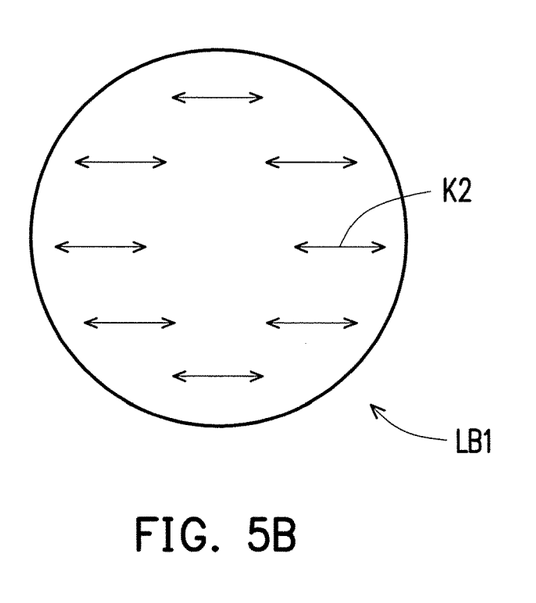

FIG. 5A and FIG. 5B are respectively schematic diagrams of cross sections of a radial polarized light and a linear polarized light. Referring to FIG. 4 to FIG. 5B, the tapered optical needle 50 of the disclosure is driven by the exciting beam LB1, wherein the exciting beam LB1 may be a radial polarized light (as shown in FIG. 5A), and enters the tapered optical needle 50 for driving the same from the bottom 120 towards the first tip T1 along a direction perpendicular to the reference plane E. A polarization direction K1 of each part of the radial polarized light surrounding a central axis of the beam is on a radial direction perpendicular to the central axis, as shown in FIG. 5A. In other embodiments, the exciting beam LB1 can also be a linear polarized light (as shown in FIG. 5B), which enters the tapered optical needle 50 for driving the same from the bottom 120 towards the first tip T1 along a direction including an angle with the reference plane E. In other words, an incident direction of the exciting beam LB1 implemented by the linear polarized light is not parallel to a direction from the first tip T1 to a center of the bottom 120, though the disclosure is not limited thereto. A polarization direction K2 of the linear polarized light is perpendicular to the central axis of the beam, and the polarization direction K2 of the entire beam is toward the same direction. When the tapered optical needle 50 is driven by the exciting beam LB1, the curved slit structure 210 may induce the surface plasmon wave on the surface plasmon wave transport layer 200, and the surface plasmon wave is focused at the second tip T2 to form a nanoscale light source LB2. To be specific, when the exciting beam LB1 enters the tapered light-transmissive needle 100, the surface plasmon wave is induced at the curved slit structure 210, and the surface plasmon wave is transported on the outer surface S2 of the surface plasmon wave transport layer 200 to form the surface plasmon resonance. Finally, the surface plasmon wave is focused at the second tip T2 to form the nanoscale light source LB2.

Figure 6A:
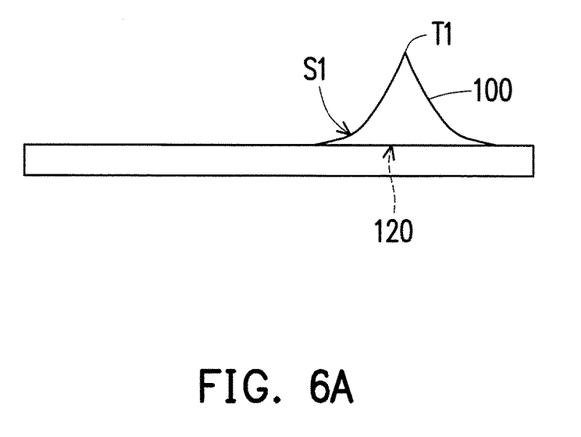
FIG. 6A to FIG. 6C illustrate a fabrication flow of a tapered optical needle according to an embodiment of the disclosure.
Figure 6B:
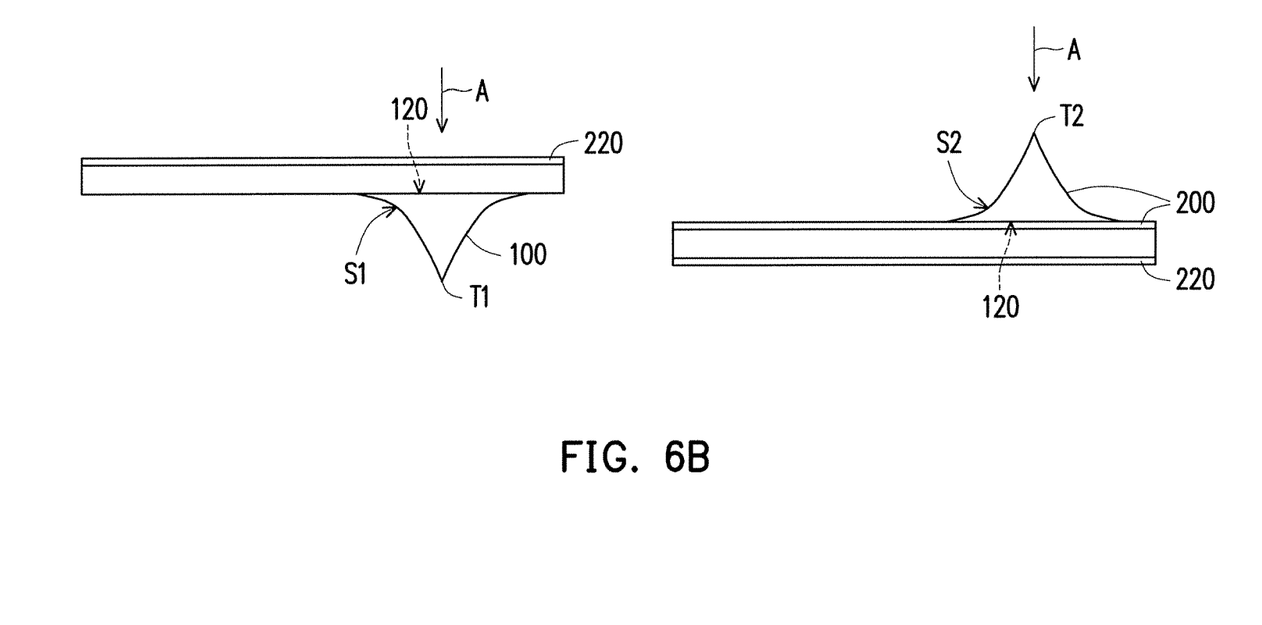
Figure 6C:
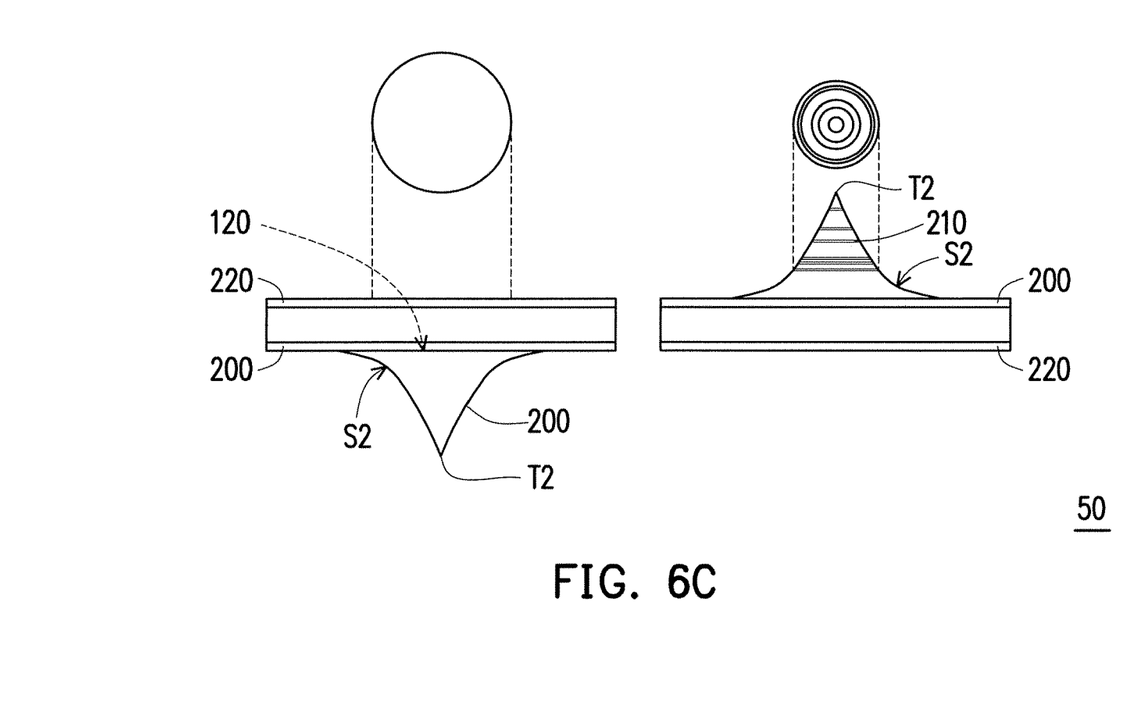

FIG. 6A to FIG. 6C illustrate a fabrication flow of a tapered optical needle according to an embodiment of the disclosure. Referring to FIG. 6A to FIG. 6C, in the fabrication steps of the tapered optical needle 50 of the disclosure, first, the tapered light-transmissive needle 100 connected to a substrate is prepared, wherein the tapered light-transmissive needle 100 can be fabricated by using silicon dioxide through a non-isotropic etching process, and the tapered light-transmissive needle 100 includes the first tip T1 and the bottom 120, as shown in FIG. 6A. Then, a reflection layer 220 and the surface plasmon wave transport layer 200 are respectively coated on the tapered light-transmissive needle 100 in a sputtering manner along a direction from the bottom 120 to the first tip T1 and a direction from the first tip T1 to the bottom 120 (a sputtering direction A shown in FIG. 6B). In the present embodiment, a material of the coated reflection layer 220 and the coated surface plasmon wave transport layer 200 is metal, for example, gold, as shown in FIG. 6B, though the disclosure is not limited thereto. Then, a focused ion beam is adopted to hollow the substrate at the bottom 120 to facilitate the exciting beam to pass. In other embodiments, the substrate at the bottom 120 is not hollowed such that the tapered optical needle 50 can be used as a probe, wherein the reflection layer 220 may serve as a reflection surface for reflecting, for example, a laser beam in an atomic force microscope (AFM). On the other hand, according to position data of the curved slit structure 210 determined in advance by using the two-dimensional simulation program according to the appearance of the curved surface S1 of the tapered light-transmissive needle 100, the focused ion beam is adopted to form the curved slit structure 210 on the curved surface S1, so as to complete the tapered optical needle 50 of the disclosure, as shown in FIG. 6C.

Figure 7:
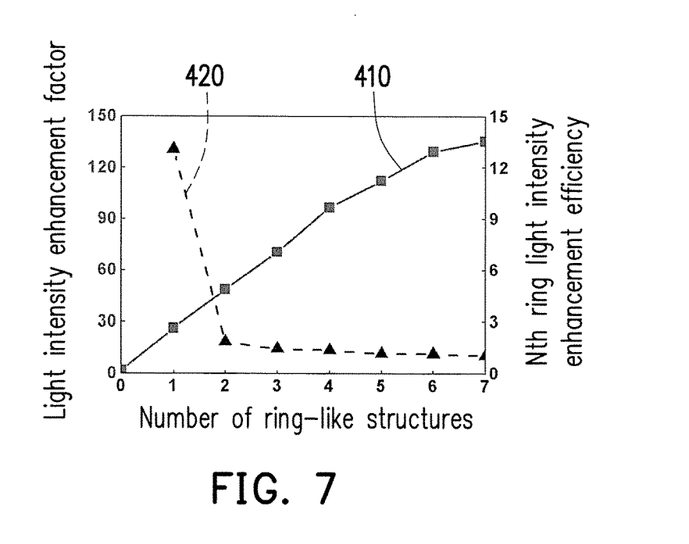
FIG. 7 is a variation broken line diagram of the number of ring-like structures of a tapered optical needle and a light intensity enhancement factor according to an embodiment of the disclosure.
Figure 8:
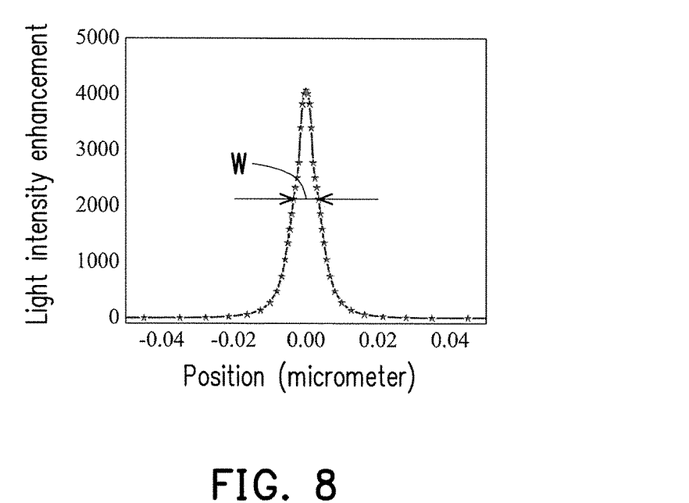
FIG. 8 is a variation curve diagram of a light intensity enhancement of a nano-light source of the light source device of FIG. 4 and a distance from the tip.

FIG. 7 is a variation broken line diagram of the number of ring-like structures of a tapered optical needle and a light intensity enhancement factor according to an embodiment of the disclosure. FIG. 8 is a variation curve diagram of a light intensity enhancement of a nano-light source of the light source device of FIG. 4 and a distance from the tip. Referring to FIG. 3A, FIG. 7 and FIG. 8, as described above, regarding the curved slit structure 210 in the tapered optical needle 50 of the disclosure, the actual position thereof is determined by the two-dimensional simulation program by adopting the radial polarized light according to a plasmon wave resonance condition. A curve 410 in FIG. 7 represents a ratio between the light intensity enhancement corresponding to the number of the ring-like structures in the curved slit structure 210 and an intensity enhancement of the exciting beam LB1:

$$E_F = \left| \frac{E_{tip}}{E_{illumination}} \right|^2$$

(enhancement factor), wherein $E_{tip}$ refers to an electric field at the second tip T2, and $E_{illumination}$ refers to an electric field of the exciting beam LB1, as shown by a left scale of FIG. 7, wherein the light intensity enhancement factor is increased along with increase of the number of the ring-like structures, and the more the number of the ring-like structures is increased, the increase of the light intensity enhancement becomes flatter. For example, when the number of the ring-like structures is 1, the light intensity enhancement factor $E_{F1}$ thereof is about 30, and when the number of the ring-like structures is 2, the light intensity enhancement factor $E_{F2}$ thereof is about 50, so that the whole light intensity enhancement can be increased by increasing the number of the ring-like structures, as shown by the curve 410 of FIG. 7. On the other hand, a curve 420 in FIG. 7 represents a light intensity enhancement efficiency $$\frac{E_{FN}}{E_{F(N-1)}}$$

(wherein $E_{FN}$ represents the $E_F$ value (i.e. the light intensity enhancement factor) in case of the N ring-like structures) obtained when the curved slit structure 210 has N ring-like structures and when the curved slit structure 210 has (N–1) ring-like structures, and the enhancement efficiency thereof is gradually flattened along with increase of the number of the ring-like structures, as shown by a right scale of FIG. 7. For example, the light intensity enhancement efficiency obtained in case that the number of the ring-like structure is 1 and the number of the ring-like structure is 0 is about 13, and the light intensity enhancement efficiency obtained in case that the number of the ring-like structure is 2 and the number of the ring-like structure is 1 is about 2. Therefore, according to the result of FIG. 7, it is learned that a difference between an enhancement effect of the tapered optical needle 50 with 7 ring-like structures and an enhancement effect of the tapered optical needle 50 with 6 ring-like structures is not large, so that the optimized tapered optical needle 50 with 6 ring-like structures has reach optical field intensity enhancement optimization. It should be noted that an electric field enhancement of a general opening-type probe is about 100 times, and the light intensity enhancement of the tampered optical needle 50 manufactured according to the disclosure may reach about 4000 times (as shown in FIG. 8), which has an enhancement effect 40 times that of the general opening-type probe, and at the second tip T2, the electric field enhancement may even reach 7000 times. On the other hand, regarding the nanoscale light source LB2 produced at the second tip T2, it is learned that a full width at half maximum (FWHM) W thereof is about 7.8 nm according to the relationship between the light intensity enhancement and the distance from the second tip T2, and since the probe used in the disclosure is a non-opening-type probe, a radius of the needle tip thereof can be reduced to improve a spatial resolution. In other words, the size of the nanoscale light source LB2 can be regarded as 7.8 nm, and the optical resolution of the tapered optical needle 50 of the disclosure may reach a size smaller than 10 nm.

The manufacturing process of the tapered optical needle 50 of the disclosure may be further combined with a microelectromechanical systems (MEMS) technique, so that the tapered optical needle 50 of the disclosure has higher stability compared to the conventional optical probe, and has higher applicability in commercial application. The tapered optical needle 50 of the disclosure can also be applied to a material detection field to serve as a probe, for example, applied to a Near-field scanning optical microscope (NSOM), a tip enhancement Raman spectroscopy (TERS) or a light-emitting diode device to use as an optical coupling structure. Namely, the tapered optical needle 50 in the embodiments of the disclosure may receive an external light signal through the second tip T2, so as to improve a measuring resolution.

In summary, in the tapered optical needle in the embodiments of the disclosure, the surface plasmon wave transport layer has the curved slit structure, so as to induce a surface plasmon wave on the surface plasmon wave transport layer. In this way, the tapered optical needle in the embodiments of the disclosure is adapted to transport the surface plasmon wave to the tip of the tapered optical needle, and form a nanofocus effect at the tip to produce a high efficiency nanoscale light source, and may improve the resolution and light emitting gain. Alternatively, the tapered optical needle in the embodiments of the disclosure is adapted to receive an optical signal from the tip of the tapered optical needle, so as to improve a measuring resolution.

Although the disclosure has been disclosed by the embodiments as the above, the disclosure is not limited thereto. Anyone having ordinary skill in the art can make various modifications and variations without departing from the scope or spirit of the disclosure. Therefore, the scope of the disclosure should be regarded as the scope defined by the following claims.

What is claimed is:

1. A tapered optical needle, comprising:
   a tapered light-transmissive needle, having a first tip, a bottom, and a curved surface connecting the first tip and the bottom; and
   a surface plasmon wave transport layer, disposed on the curved surface and entirely covering the first tip, wherein the surface plasmon wave transport layer has a curved slit structure to expose a part of the curved surface, the curved slit structure comprises a plurality of curved portions arranged from the first tip to an edge of the bottom and located between the first tip and the edge of the bottom, and extending directions of the curved portions are different to a direction from the first tip to the edge of the bottom.

2. The tapered optical needle as claimed in claim 1, wherein the tapered optical needle is driven by an excitation light source, and a surface plasmon wave is induced at the curved slit structure, and the curved portions are located at positions producing a surface plasmon resonance at a surface of the surface plasmon wave transport layer facing away from the tapered light-transmissive needle, and a nanoscale light source is formed by focusing at one end of the surface plasmon wave transport layer facing away from the first tip.

3. The tapered optical needle as claimed in claim 2, wherein the excitation light source provides a radial polarized light to drive the tapered optical needle.

4. The tapered optical needle as claimed in claim 2, wherein the excitation light source provides a linear polarized light to the tapered optical needle to drive the tapered optical needle, and an incident direction of the linear polarized light is not parallel to a direction from the first tip to a center of the bottom.

5. The tapered optical needle as claimed in claim 1, wherein the tapered light-transmissive needle is a circularly symmetric tapered structure.

6. The tapered optical needle as claimed in claim 5, wherein the curved surface is a quasi-parabolic surface.

7. The tapered optical needle as claimed in claim 1, wherein a material of the tapered light-transmissive needle comprises silicon dioxide.

8. The tapered optical needle as claimed in claim 7, wherein a material of the surface plasmon wave transport layer is metal.

9. The tapered optical needle as claimed in claim 1, wherein a material of the tapered light-transmissive needle comprises silicon.

10. The tapered optical needle as claimed in claim 9, wherein the surface plasmon wave transport layer is a semiconductor material.

11. The tapered optical needle as claimed in claim 1, wherein one end of the surface plasmon wave transport layer facing away from the first tip is a second tip, a distance between the second tip and the curved portion closest to the second tip among the curved portions and distances between the adjacent curved portions are all different.

12. The tapered optical needle as claimed in claim 11, wherein the tapered optical needle is driven by an excitation light source, a distance L between the second tip and each of the curved portions arranged from the second tip to the edge of the bottom in the curved slit structure satisfies:

$$0 < L \le \frac{1}{2k''_{sp}}, \text{ and } k_{sp} = k'_{sp} + ik''_{sp} = \left[\frac{\omega}{c}\left(\frac{\varepsilon_1 \varepsilon_2}{\varepsilon_1 + \varepsilon_2}\right)^{1/2}\right],$$

wherein $k_{sp}$ is a wave vector constant of the surface plasmon wave, $k'_{sp}$ and $ik''_{sp}$ are respectively a real part and an imaginary part of $k_{sp}$, $\omega$ is a frequency of the excitation light source, c is a light speed, $\varepsilon_1$ is a dielectric coefficient of the surface plasmon wave transport layer, $\varepsilon_2$ is a real part of a dielectric coefficient of the tapered light-transmissive needle.

13. The tapered optical needle as claimed in claim 1, wherein a distance between a center of an orthogonal projection of the curved slit structure on a reference plane parallel to the bottom and an orthogonal projection of the first tip on the reference plane is not more than 1/10 of a wavelength of an excitation light source used for driving the tapered optical needle.

* * * * *